United States Patent [19]
Shiraishi et al.

[11] Patent Number: 6,024,563
[45] Date of Patent: Feb. 15, 2000

[54] OCCLUSION OBSERVING DEVICE

[75] Inventors: Kazuo Shiraishi, Yuki; Akihiko Tashiro, Omiya; Tadashi Kimura, Kurashiki, all of Japan

[73] Assignee: Sankin Kogyo Kabushiki Kaisha, Tochigi, Japan

[21] Appl. No.: 08/891,026

[22] Filed: Jul. 10, 1997

[30] Foreign Application Priority Data

Jul. 10, 1996 [JP] Japan .................................. 8-180699

[51] Int. Cl.⁷ .................................................. A61C 11/00
[52] U.S. Cl. ...................................................... 433/55
[58] Field of Search ................................ 433/55, 56, 69, 433/73

[56] References Cited

U.S. PATENT DOCUMENTS 4,619,611  10/1986  Shimbashi ................................ 433/55
4,773,854   9/1988  Weber ..................................... 433/73

*Primary Examiner*—John J. Wilson
*Attorney, Agent, or Firm*—Skjerven, Morrill, MacPherson, Franklin & Friel LLP

[57] ABSTRACT

A device which allows easy observation of discrepancies between the upper and lower jaw comprises an upper bow (100) and a lower bow (200) which separately hold in place an upper jaw model (UM) and a lower jaw model (LM) prepared based on impressions and position these upper and lower jaw models (UM) and (LM) opposite to each other, checker pins (310) in the upper bow (200) which are positioned at a location corresponding to the opening/closing axis of the upper jaw model (UM) and lower jaw model (LM) and along the opening/closing axis, and checker plates (300) in the upper bow (100) positioned in such a manner that their outer surfaces (306) are perpendicular to the opening/closing axis and adjacent to the tips of the checker pins (310).

3 Claims, 6 Drawing Sheets

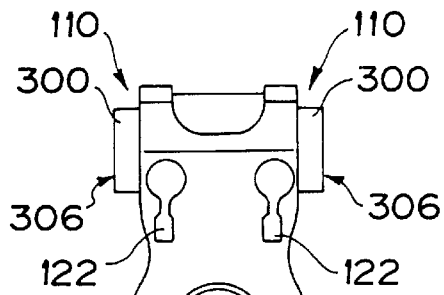
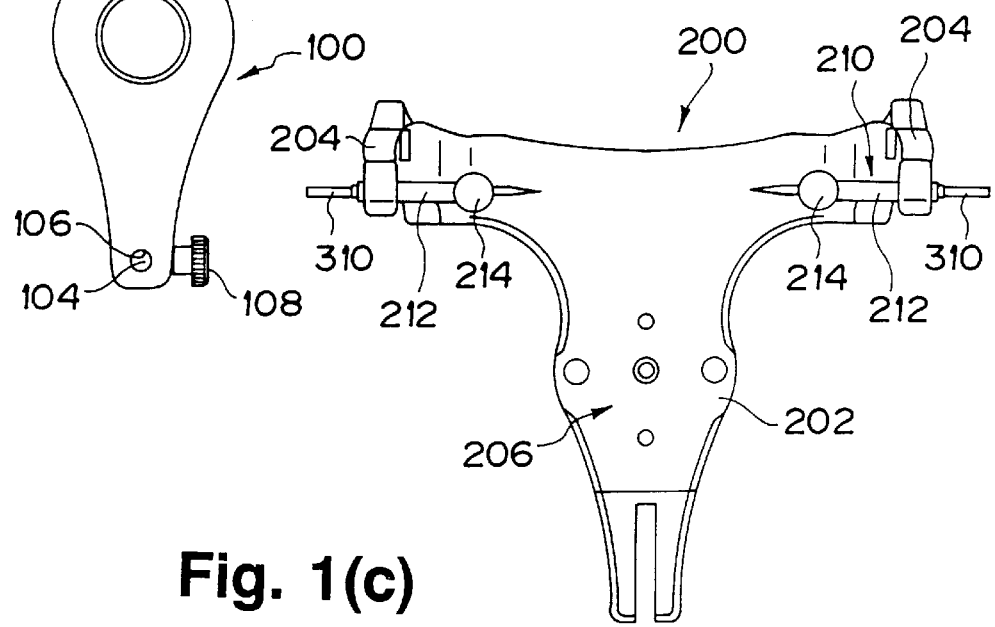
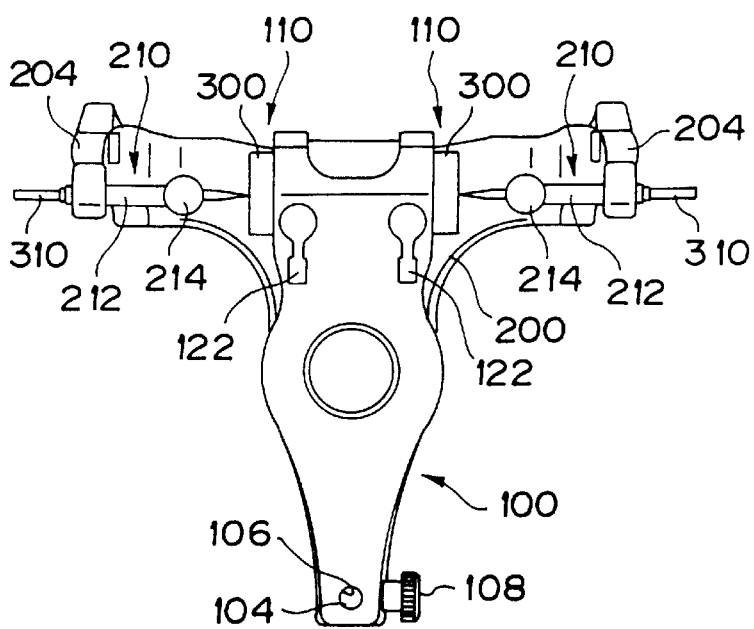

OCCLUSION OBSERVING DEVICE

BACKGROUND OF THE INVENTION

1. Field of the Invention

The present invention concerns a device for observing discrepancies between the upper and lower jaw.

2. Description of the Related Art

The relative positions between the upper and lower jaws may change depending on the situation where the jaws are in a mutually centric position, i.e., with the cusps of the teeth not fitting together in a resting position, or the situation where they are in a position with the cusps of the teeth fitting together.

It is rare that the patient is aware of such change or discrepancies between the upper and lower jaw, and in many cases, such discrepancies are discovered by the dentist, dental technician, etc. in the course of designing dentures. Specifically, when dentists, dental technicians, etc. design dentures, after models of both the upper and lower jaw have been prepared based on impressions taken from the patient, a specialized device referred to as an articulator is used to place the upper and lower jaw models in a centric position and in a position with the cusps of the teeth fitting together in order to determine the discrepancy between the upper and lower jaw.

In cases where the discrepancy between the upper and lower jaw is extremely small, there is no particular problem with leaving this discrepancy untreated, but in cases where the discrepancy is great enough to exceed the allowable range, a burden is applied on the temporomandibular joint during chewing, and there may be a risk of causing damage to the jaw, such as temporomandibular disorder, it is preferable to carry out occlusal therapy at an early stage whenever possible.

In the past, however, as there was no way to allow the patient to easily observe the status of the discrepancy between the upper and lower jaw, e.g., the direction and amount of this discrepancy, this constituted a severe drawback with respect to the patient's informed consent to treatment, so the condition was left untreated.

SUMMARY OF THE INVENTION

In view of the above situation, an objective of the present invention is to solve the above-described problem, and to provide a device capable of allowing easy observation of the status of discrepancies between the upper and lower jaw.

According to the present invention, an occlusion observing device comprises a pair of model holders for separately holding in place an upper jaw model and a lower jaw model prepared based on impressions taken from a patient, and for positioning the upper and lower jaw models opposite to each other; pointer means provided in one of the model holders at a location corresponding to an opening/closing axis of the upper and lower jaw models and in alignment with the opening/closing axis; and an indicator surface provided in another of the model holders positioned perpendicular to the opening/closing axis and adjacent to a tip of the pointer means.

In the device of this construction, it is preferable that there are provided with a pair of the pointer means and a pair of indicator surfaces, with the pair of pointer means and the pair of indicator surfaces being respectively arranged symmetrically with respect to a median plane of the upper and lower jaw models.

As the present invention allows easy observation of discrepancies between the upper and lower jaw by means of discrepancies in the pointer components with respect to the indicator surfaces, this makes it possible, for example, for the dentist and patient to work towards achieving informed consent to early occlusal treatment.

Further, the occlusion observing device may further comprise shaft means secured on said one of the model holders with an axis thereof being aligned with the opening/closing axis, and formed with a pointer insertion hole along the axis thereof, into which the pointer means is inserted in such a way that the pointer means can be moved forward and backward; indicator means having a flat surface; bearing means which can be detachably engaged on outer periphery of the shaft means and which, when engaged, can be rotated around the axis of the shaft means; and selective holding means for alternatively and detachably holding in place the indicator means and bearing means with respect to said another of the model holders, wherein when the bearing means are held in place on said another of the other model holders by way of the selective holding means and the bearing means are engaged with the shaft means, the upper and lower jaw models are positioned opposite to each other in a mutually centric position, and the pair of model holders are supported such that they can swing with the opening/closing axis being as a center of swing; and when the indicator means is held in place on said another of the model holders by way of the selective holding means and the pointer means is inserted into the pointer insertion hole of the bearing means, the flat surface of the indicator means serves as the indicator surface.

In the device of the above construction, it is preferable that there are provided a pair of the shaft means, a pair of indicator means, a pair of bearing means and a pair of selective holding means, with the pair of shaft means and the pair of selective holding means being respectively arranged symmetrically with respect to a median plane of the upper and lower jaw models.

BRIEF DESCRIPTION OF THE DRAWINGS

FIGS. 1(a) through 1(c) are conceptual diagrams of an embodiment of the occlusion observing device of the present invention, with FIG. 1(a) being a plan view showing one of the model holders, FIG. 1(b) being a plan view showing the other model holder, and FIG. 1(c) being a plan view showing how the pair of model holders are positioned;

DESCRIPTION OF THE PREFERRED EMBODIMENTS

Figure 2:
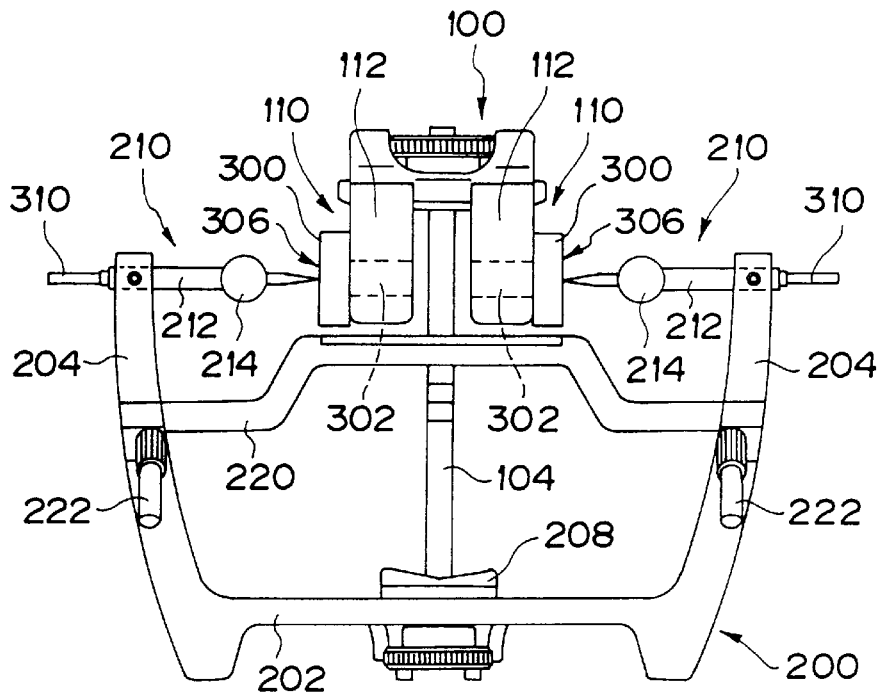
FIG. 2 is a rear view of the occlusion observing device shown in FIGS. 1(a) to 1(c)

The embodiment of the present invention will now be described in reference to the accompanying drawings.

FIGS. 1(a) through 3 are conceptualized diagrams of an embodiment of the occlusion observing device of the present invention. The occlusion observing device allows the patient to observe discrepancies between the upper and lower jaw using upper and lower jaw models UM and LM which have been fabricated based on impressions taken from the patient, and comprises an upper bow 100 for holding the upper jaw model UM in place and a lower bow 200 for holding the lower jaw model LM in place.

The upper bow 100 corresponds to the patient's maxilla, and is in the form of a plate extending in a front/back direction (upward/downward direction in FIG. 1(a)) having a flat installation bottom face 102 at its central portion for mounting an upper jaw mounting plate 150. At the upper bow 100, an incisor pin 104 is disposed at a position forward from the mounting base plate 102, and a pair of selective holding means 110 is disposed at a position to the rear of the mounting base plate 102.

The incisor pin 104 is perpendicular to the extension direction of the mounting base plate 102 and protrudes downward from the lower surface of the front end of the upper bow 100. It constitutes a cylindrical shape having a uniform external diameter, and after it is inserted into a pin insertion hole 106 formed in the upper bow 100, it protrudes into the pin insertion hole 106 and can be tightened into place using a pin mounting screw 108 which is screwed into the upper bow 100, thus making it possible to adjust the distance by which it protrudes from the lower surface of the upper bow 100. The incisor pin 104 is detachably disposed with respect to the upper bow 100.

Figure 3:
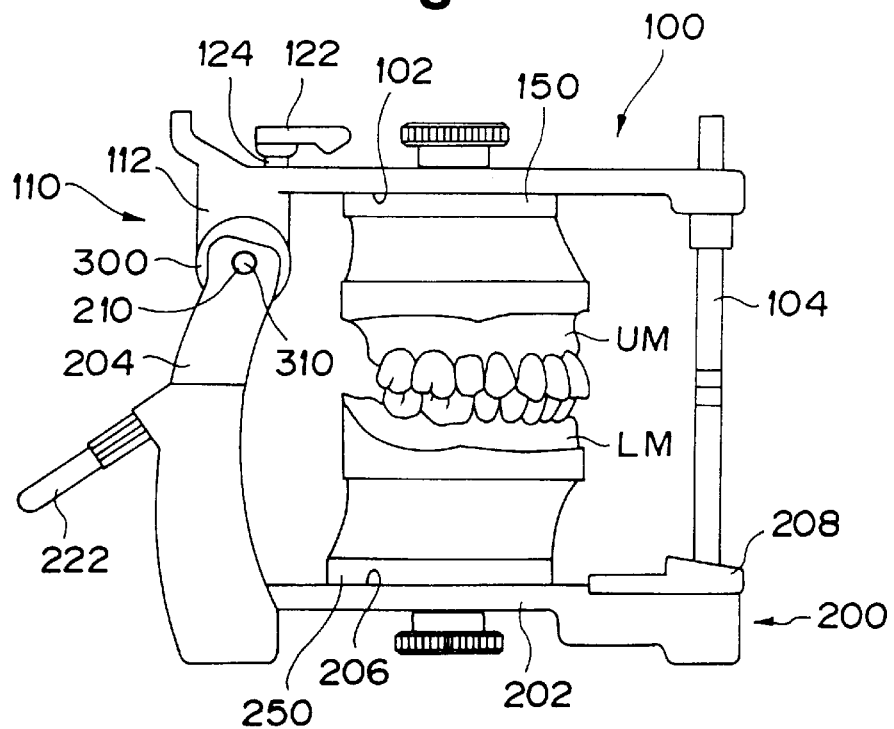
FIG. 3 is a lateral view showing the upper and lower jaw models held in place in the occlusion observing device shown in FIG. 1(a)
Figure 4:
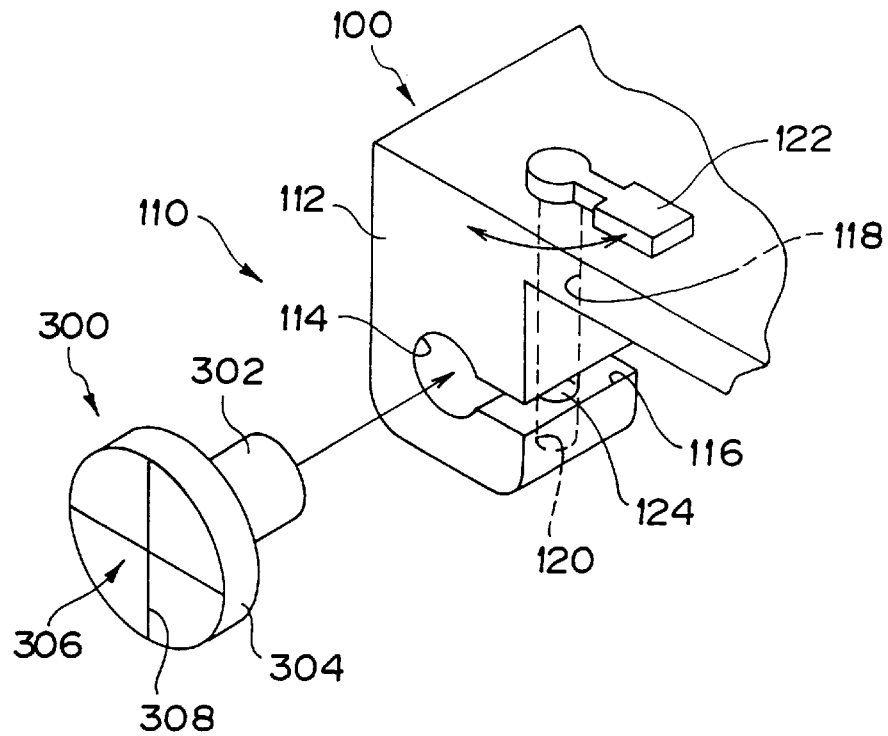
FIG. 4 is an exploded oblique view of the essential components showing the configuration of the indicator components used in the occlusion observing device shown in FIGS. 1(a) to 1(c)

As shown in FIGS. 2 through 4, the pair of selective holding means 110 comprises a pair of rectangular blocks 112 which are arranged so as to extend downward from the lower surface of the upper bow 100 on the right and left sides, a pair of selective mounting holes 114 which penetrate the rectangular blocks 112 and the axial centers of which are aligned in a horizontal direction, a pair of adjustment notches 116 formed so as to open into the selective mounting holes 114 from a position corresponding to the axial center of the selective mounting holes 114 in the front end surface of the rectangular blocks 112, a pair of bolt receiving holes 118 formed so as to open from the upper surface of the upper bow 100 into the adjustment notches 116, a pair of screw holes 120 formed with their axial centers aligned in the extension area of the bolt receiving holes 118, and a pair of detachable operating bolts 124, the ends of which are screwed into corresponding screw holes 120 from the upper surface of the upper bow 100 through the bolt receiving holes 118 and which have operating levers 122 installed on their upper ends.

In the pair of selective holding means 110, when the detachable operating bolts 124 have been rotated as appropriate via the operating levers 122, this makes it possible to change the separation of the adjustment notches 116 so as to expand/contract the internal diameter of the selective mounting holes 114 formed in the rectangular blocks 112.

On the other hand, the lower bow 200 of the occlusion observing device, as shown in FIGS. 1(a) through 3, corresponds to the mandible of the patient, and comprises a plate component 202 corresponding to the upper bow 100 and a pair of arms 204 which are extended in an upward direction from both sides of the back of the plate component 202.

The plate component 202 is in the form of a plate which is extended in a forward/backward direction, and it has a flat upper surface 206 for mounting of a lower jaw mounting plate 250 at its central portion. An incisor table 208 is disposed on the lower bow 200 at a position in front of the flat upper surface 206. The upper surface of the incisor table 208 is arranged in such a manner that it gradually slopes downward from the right and left sides toward the center, and it is configured so as to be detachable with respect to the lower bow 200.

When viewed from the front, the arms 204 form a shortened U shape opening upward, and shaft components 210 are held in place on the respective upper ends of these arms.

As shown in FIGS. 1(c) and 2, the shaft components 210 comprise shafts 212 of a cylindrical shape and spherical heads 214 attached to the ends of these shafts 212. The spherical heads 214 are positioned facing each other in such a way as to leave sufficient space between them for the rear ends of the upper plate 100, the axial centers of the shafts 212 are mutually aligned in a horizontal direction, and the spherical heads are fixed via the shafts 212 that are inserted into the shaft mounting holes 216 formed in the arms 204.

Figure 5:
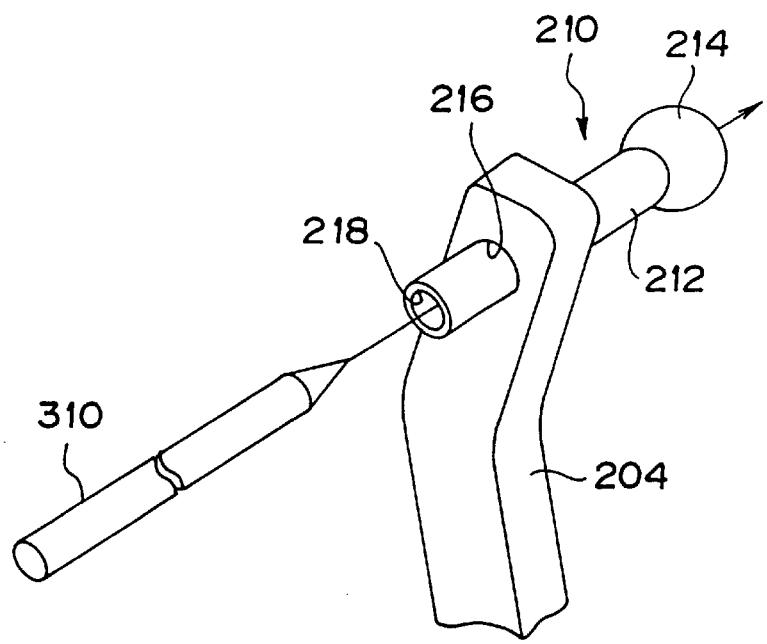
FIG. 5 is an exploded oblique view of the essential components showing the configuration of the pointer components used in the occlusion observing device shown in FIGS. 1(a) to 1(c)

As shown in FIG. 5, pointer insertion holes 218 are formed in the pair of shaft components 210 in positions along the axial center of the shafts 212. The pointer insertion holes 218 pass through the shaft components 210 across an area extending from the base surface of the shafts 212 to the outer surface of the spherical heads 214. Moreover, reference numeral 220 in FIG. 2 designates a connecting component which links the pair of arms 204, and reference numeral 222 designates legs arranged in a detachable manner on the rear surface of the arms 204 in such a way that they will gradually incline downward toward backward direction.

Moreover, as shown in FIGS. 1(a), 1(c), 4, 7 and 8, the occlusion observing device also comprises a pair of checker plates (indicator components) 300, a pair of checker pins (pointer components) 310, and a pair of bearings 320.

The checker plates 300, as shown in FIGS. 2 and 4, comprise cylindrical plate mounting column components 302 which have an external diameter allowing them to fit into the selective mounting holes 114 of the selective holding means 110 and disk-shaped indicator plates 304 having a diameter which is sufficiently larger than that of the plate mounting column components 302 and mounted on one end of the plate mounting column components 302 in such a way that their axial centers are aligned, and it has cross lines 308 centered on the axis on the outer surface (indicator surface) of the indicator plates 304.

The checker pins 310, as shown in FIGS. 2 and 5, are in a cylindrical shape with a diameter smaller than that of the pointer insertion holes 218 formed in the shaft components 210, their ends are in the form of sharp points, and they are of sufficient length so that both of their ends protrude outward when they are inserted into the pointer insertion holes 218.

Figure 7:
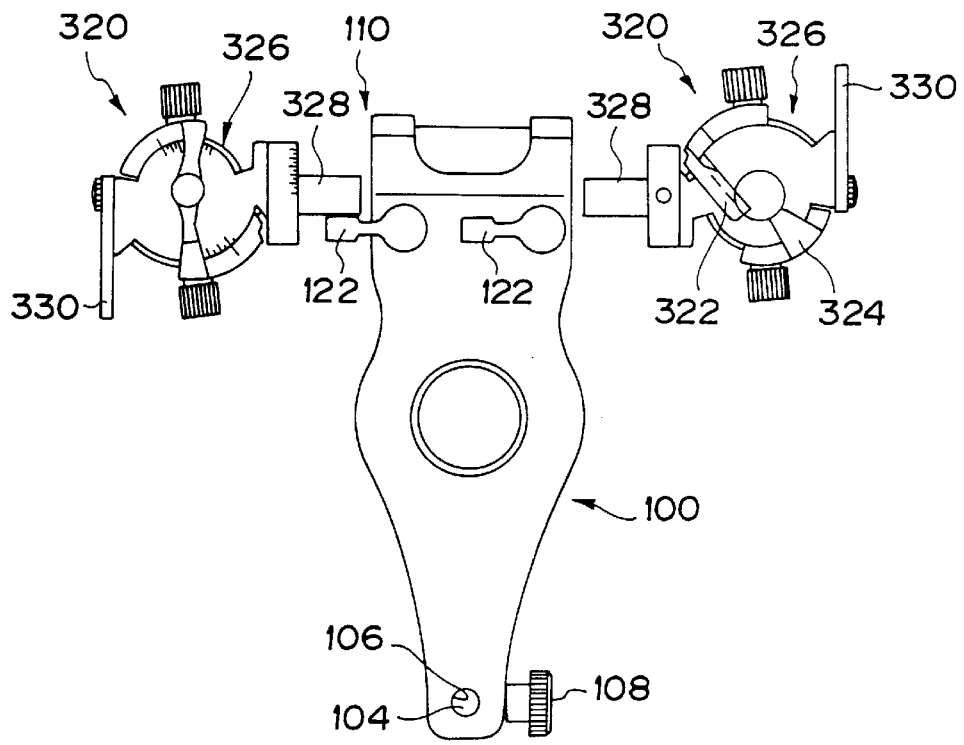
FIG. 7 is an exploded plan view showing the configuration of the bearing components used in the occlusion observing device shown in FIGS. 1(a) to 1(c)
Figure 8:
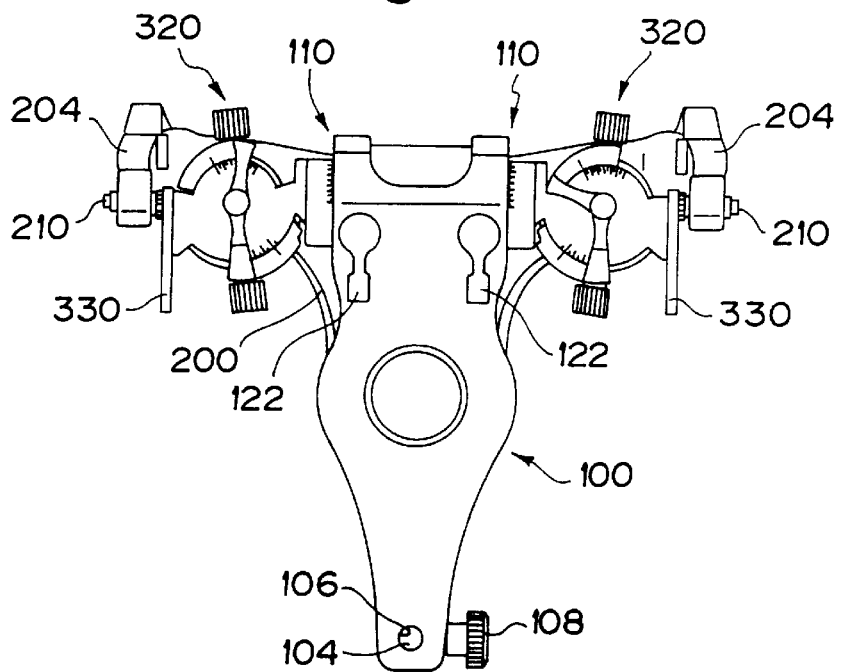
FIG. 8 is a plan view showing the bearing components and shaft components of the occlusion observing device shown in FIGS. 1(a) to 1(c) in an engaged position.
Figure 9:
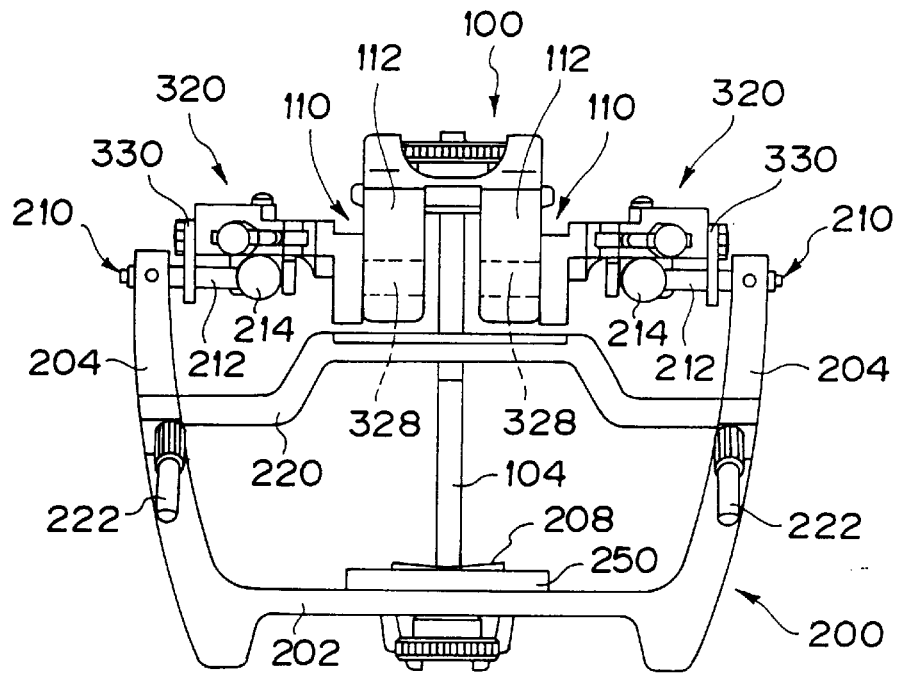
FIG. 9 is a rear view showing the bearing components and shaft components of the occlusion observing device shown in FIGS. 1(a) to 1(c) in an engaged position.

As shown in FIG. 7, the bearing components 320 comprise spherical head supporting pieces 326 referred to as fossa boxes having two control blocks 322 and 324 each, bearing mounting column components 328 which can be extended from one end of the spherical head supporting pieces 326 and which are of the same shape as the plate mounting column components 302 of the checker plates 300, and hook-shaped centric latches 330 (not shown in the figures) which are positioned on the other end of the spherical head supporting pieces 326 in such a way that they can swing and are at locations close to the respective vibration centers. As shown in FIGS. 8 and 9, when they are engaged with the shaft components 210 via the hook-shaped components (not shown in the figures) of the centric latches 330 in such a way that the cylindrical heads 214 of the bearing components 320 are positioned in the control blocks 322 and 324 of the cylindrical head supporting components 326, they are supported in such a way that they can be rotated around the axial center of the shaft components 210 with the axial centers of the bearing mounting column components 328 being aligned with the axial center of the bearing components 320.

As shown in FIG. 7, in the occlusion observing device having the above configuration, the bearing mounting column components 328 of the bearing components 320 are inserted in the selective mounting holes 114 of the upper bow 100 with the detachable operating bolts 124 in a relaxed position, and after this, by tightening the detachable operating bolts 124, the pair of bearing components 320 can be held in place on the upper bow 100.

As shown in FIGS. 8 and 9, when the centric latches 330 are operated from this configuration and when the bearing components 320 held in place on the upper bow 100 are supported by the shaft components 210 of the lower bow 200, the upper bow 100 is supported in such a way that it can swing with respect to the lower bow 200 centered around the axial center of the shaft components 210.

Figure 10:
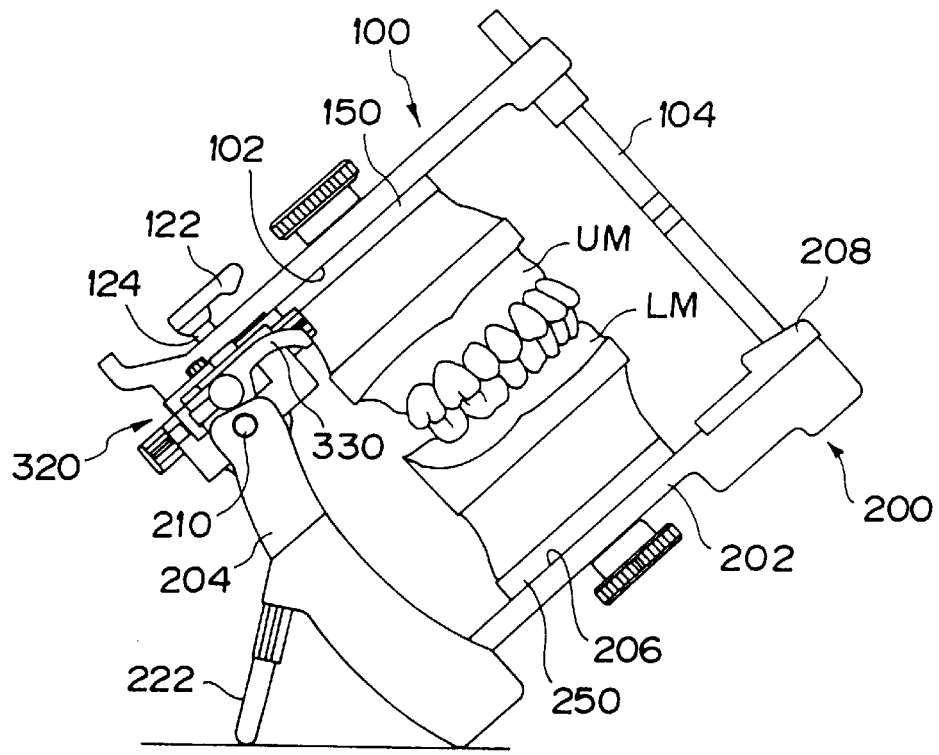
FIG. 10 is a lateral view showing the bearing components and shaft components of the occlusion observing device shown in FIGS. 1(a) to 1(c) in an engaged position and the upper and lower jaw models held in place.

Moreover, as shown in FIG. 10, using a suitable dedicated device such as a check bite in the configuration described above, with the axial center of the shaft components 210 being the actual opening/closing axis of the jaw, the upper jaw model UM is held in place on the mounting base plate 102 of the upper bow 100 via the mounting plate for upper jaw use 150, the lower jaw model LM is held in place on the flat upper surface 206 of the lower bow 200 via the mounting plate 250 for lower jaw, and the length of the incisor pin 104 can be adjusted as appropriate in order to position these upper and lower jaw models UM and LM in a mutually centric position.

When the occlusion observing device is in this position and the upper bow 100 is caused to swing with respect to the lower bow 200, the upper jaw model UM is mounted so as to open and close with respect to the lower jaw model LM. On the other hand, the mounting direction of the bearing components 320 with respect to the upper bow 100 is adjusted as appropriate. Moreover, after the positions of the two control blocks 322 and 324 of the spherical head supporting components 326 have been adjusted as appropriate with respect to the spherical heads 214 of the bearing components 210, when the centric latches 330 are released, as it becomes possible to reproduce the discrepancy between the upper and lower jaw when the patient actually bites down, the unit can be used as a semi-adjustable articulator of the type conventionally used to confirm occlusion in designing dentures.

In this connection, as shown in FIG. 10, if the occlusion observing device is placed on a table supported by the rear edge of the upper bow 200 and the pair of legs 222, it is possible to observe more easily the upper and lower models UM and LM, and the procedure described above can be carried out more efficiently.

After the upper and lower jaw models UM and LM have been fixed in place on the upper bow 100 and lower bow 200, the centric latches 330 are now released to separate the upper bow 100 from the lower bow 200, and in the opposite procedure from the above, the bearing components 320 are detached from the upper bow 100.

Next, as shown in FIG. 4, the plate mounting column components 302 of the checker plates 300 are inserted into the selective mounting holes 114 of the upper bow 110, and after this, by tightening the detachable operating bolts 124, the pair of checker plates 300 can be held in place on the upper bow 100.

Moreover, as shown in FIGS. 1(c) and 5, in the lower bow 200 which has been detached from the upper bow 100, the checker pins 310 are inserted into the pointer insertion holes 218 of the shaft components 210 from the outside with their pointed tips facing each other.

Figure 6A:
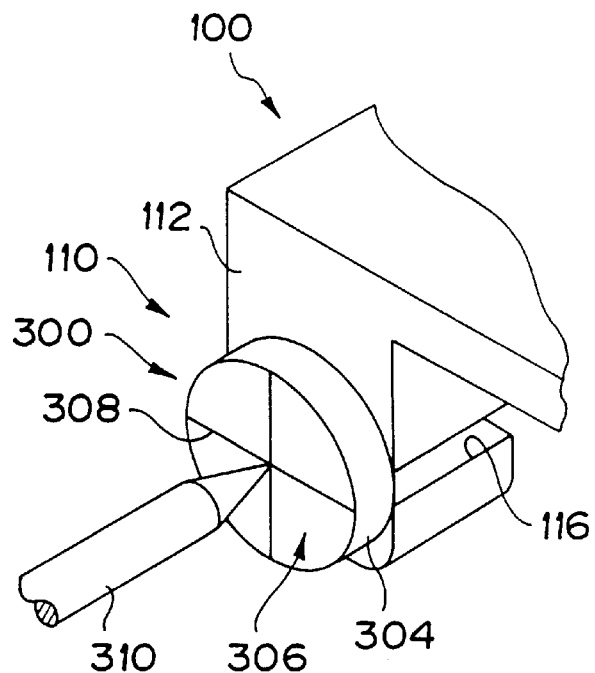
FIGS. 6(a) and 6(b) are configuration diagrams of the pointer components and indicator surfaces in the occlusion observing device shown in FIGS. 1(a) to 1(c), with FIG. 6(a) being an exploded diagram of the essential components showing the components in a centric position and FIG. 6(b) being an exploded diagram of the essential components with the cusps of the teeth fitting together.

When the upper bow 100 is positioned on the upper portion of the lower bow 200 from the configuration described above and the upper and lower jaw models UM and LM are positioned opposite to each other, these upper and lower jaw models UM and LM are again in a mutually centric position, and at this point, as shown in FIG. 6(a), the tips of the checker pins 310 point to the center of the cross lines 308 printed on the outer surfaces 306 of the checker plates 300.

Figure 6B:
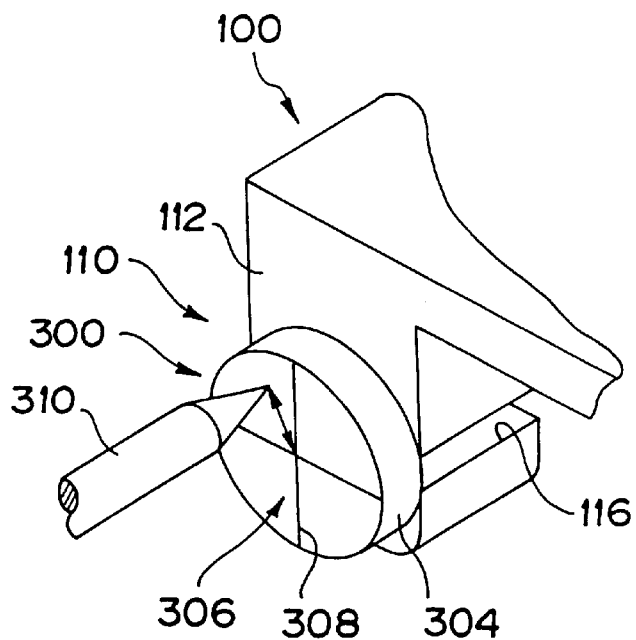

From this configuration, when the upper jaw model UM and lower jaw model LM are positioned with the cusps of the teeth fitting together, if a discrepancy occurs between the upper and lower jaw models UM and LM, as shown in FIG. 6(b), the direction and amount of this discrepancy appears as a discrepancy of the checker pins 310 with respect to the outer surface 306 of the checker plates 300.

Accordingly, when the above operation is performed in the presence of the patient, it becomes possible for the patient to easily observe the discrepancy between the upper and lower jaw by means of the discrepancy in the checker pins 310 with respect to the outer surface 306 of the checker plates 300, and it thus becomes possible for the dentist and patient to work towards achieving informed consent with respect to early occlusal treatment.

Moreover, in the embodiment described above, the indicator surface is located in the model holder which holds the upper jaw model in place and the pointer component is located in the model holder which holds the lower jaw in place. Alternatively, the opposite configuration is also possible, i.e., with the pointer component located in the model holder which holds the upper jaw in place and the indicator surface located in the model holder which holds the lower jaw model in place. In this case, it is not absolutely necessary to have a pair of indicator components, and one may also use a single pointer component having both ends in the form of sharp points. Moreover, although the indicator surface is located on the outer end surface of the indicator component in this configuration, the indicator surface may also be directly located on the model holder.

Furthermore, in the embodiment described above, the indicator component comprising the indicator surface is installed in a detachable manner with respect to one of the model holders, the pointer component is installed in a detachable manner with respect to the other model holder, and the device is configured in such a way that the bearing component may be installed instead of the indicator component. Therefore, as mentioned above, the occlusion observing device may also be used of an articulator. However, in cases where use of an articulator is not necessary, the indicator component and pointer component may of course be configured in such a way that they are attached to the model holders. In this case, the bearing components are not needed.

What is claimed is:

1. An occlusion observing device comprising:
   a pair of model holders for separately holding in place an upper jaw model and a lower jaw model prepared based on impressions taken from a patient, and for positioning the upper and lower jaw models opposite to each other;
   shaft means secured on one of the model holders at a portion in alignment with an opening/closing axis of the upper and lower jaw models, and formed with a pointer insertion through-hole along an axis thereof;
   pointer means disposed into the pointer insertion through-hole of the shaft means;
   indicator means having an indicator surface;
   bearing means which can be detachably engaged on the outer periphery of the shaft means and which, when engaged, can be rotated around the axis of the shaft means; and;
   selective holding means for alternatively and detachably holding in place the indicator means and bearing means with respect to another of the model holders;
   wherein when the bearing means are held in place on said another of the model holders by way of the selective holding means and the bearing means are engaged with the shaft means, the upper and lower jaw models are positioned opposite to each other in a mutually centric position, and the pair of model holders are supported such that they can swing with the opening/closing axis being as a center of swing; and
   when the indicator means is held in place on said another of the model holders by way of the selective holding means, the indicator surface of the indicator means is positioned perpendicular to the opening/closing axis and adjacent to a tip of the pointer means.

2. The occlusion observing device according to claim 1, wherein the shaft means, the bearing means and the selective holding means are provided in a pair, respectively, with the pair of shaft means and the pair of selective holding means being respectively arranged symmetrically with respect to a median plane of the upper and lower jaw models.

3. The occlusion observing device according to claim 2, wherein the pointer means and the indicator means are provided in a pair, respectively, with the pair of pointer means and the pair of indicator means being respectively arranged symmetrically with respect to the median plane of the upper and lower jaw models.

* * * * *